US011776670B1

(12) United States Patent
Walk et al.

(10) Patent No.: US 11,776,670 B1
(45) Date of Patent: Oct. 3, 2023

(54) SYSTEM AND METHOD FOR FACILITATING EMPLOYEE HEALTH SCREENING USING AN APPLICATION ON A MOBILE COMPUTING DEVICE

(71) Applicant: WM INTELLECTUAL PROPERTY HOLDINGS, L.L.C., Houston, TX (US)

(72) Inventors: Erika Walk, Houston, TX (US); Abhishek Patni, Houston, TX (US)

(73) Assignee: WM INTELLECTUAL PROPERTY HOLDINGS, L.L.C., Houston, TX (US)

( * ) Notice: Subject to any disclaimer, the term of this patent is extended or adjusted under 35 U.S.C. 154(b) by 0 days.

(21) Appl. No.: 17/833,496

(22) Filed: Jun. 6, 2022

Related U.S. Application Data

(60) Provisional application No. 63/294,136, filed on Dec. 28, 2021.

(51) Int. Cl.
| | | |
|---|---|---|
| *G16H 10/20* | (2018.01) | |
| *G16H 50/30* | (2018.01) | |
| *G07C 9/33* | (2020.01) | |
| *G16H 10/60* | (2018.01) | |
| *G16H 80/00* | (2018.01) | |

(52) U.S. Cl.
CPC ............. *G16H 10/20* (2018.01); *G07C 9/33* (2020.01); *G16H 10/60* (2018.01); *G16H 50/30* (2018.01); *G16H 80/00* (2018.01)

(58) Field of Classification Search
None
See application file for complete search history.

(56) References Cited

U.S. PATENT DOCUMENTS

| | | | |
|---|---|---|---|
| 2021/0012254 A1* | 1/2021 | Campbell | G06Q 30/0185 |
| 2021/0290177 A1* | 9/2021 | Novak, Jr. | A61B 5/6826 |
| 2021/0296008 A1* | 9/2021 | Novak, Jr. | A61B 5/0022 |
| 2021/0327187 A1 | 10/2021 | Wisniewski | |
| 2021/0328801 A1* | 10/2021 | Sly | H04L 9/0894 |
| 2021/0335074 A1* | 10/2021 | Cowles | G07C 9/27 |
| 2021/0335458 A1* | 10/2021 | McMullen | G06K 7/1095 |

(Continued)

FOREIGN PATENT DOCUMENTS

| | | | | |
|---|---|---|---|---|
| WO | 2021/207240 | | 10/2021 | |
| WO | WO-2021207240 A1 * | 10/2021 | | A61B 5/0022 |

OTHER PUBLICATIONS

Access Protocols for All State Offices and Facilities (2020), https://dbm.maryland.gov/employees/Documents/COVID-19%20Building%20Entry%20Protocol.pdf (last visited Aug. 2, 2023) (Year: 2020).*

(Continued)

*Primary Examiner* — Jonathon A. Szumny
*Assistant Examiner* — Nicholas Akogyeram, II
(74) *Attorney, Agent, or Firm* — Greenberg Traurig LLP

(57) ABSTRACT

A system and method for facilitating employee health screening using an application on a mobile computing device are provided. The system and method can provide a centralized platform for providing a health screening questionnaire for employees to fill out before visiting an employer's facility. The system and method can perform an employee badge activation/deactivation function based on one or more indicators relating to employee health information.

12 Claims, 3 Drawing Sheets

(56) References Cited

U.S. PATENT DOCUMENTS

2021/0338102 A1* 11/2021 Palacios ............... A61B 5/0075
2021/0375084 A1* 12/2021 Aubrey .................... G07C 9/27

OTHER PUBLICATIONS

VMWare, Employee Experience When They Receive a Health Attestation Notification in Workspace ONE Intelligent Hub App, Sep. 1, 2021.
Crowdblink, Employee Health Screening App: Daily Covid-19 Assessments, Nov. 19, 2021.
USCF, Daily Health Screening, Nov. 19, 2021; 3 pages.
Returnsafe, Health Screening Prior to Entering the Workplace, Nov. 19, 2021.
Goevo, Return to work safely and quickly with the Personal Protective App (PPA), Dec. 31, 2021.
Microsoft, Use the Employee Return to the Workplace app, Aug. 3, 2021.
Servicenow, Configure Employee Health Screening, Dec. 31, 2021.
Higley, Card Access Data Integration and Reporting During COVID-19, Aug. 31, 2020.
Ryerson, Introducing RyersonSafe for health screening process for all students, faculty, staff, visitor, Jul. 12, 2021.

* cited by examiner

SYSTEM AND METHOD FOR FACILITATING EMPLOYEE HEALTH SCREENING USING AN APPLICATION ON A MOBILE COMPUTING DEVICE

RELATED APPLICATIONS

This application claims the benefit, and priority benefit, of U.S. Provisional Patent Application Ser. No. 63/294,136, filed Dec. 28, 2021, the disclosure and contents of which are incorporated by reference herein in their entirety.

BACKGROUND

Field of Invention

The presently disclosed subject matter relates generally to health screening, and more specifically, to facilitating employee health screening using an application on a mobile computing device.

Description of the Related Art

Traditional systems and methods for employee health screening prior to entering an employer facility involve, e.g., quick response or "QR" codes as an entry pass after the employee health screening is completed and/or "day pass" approaches for employee badge activity.

These long standing systems and methods present logistical and other challenges for employers. For example, using QR codes requires additional infrastructure at the work location to scan the codes so the employees can be granted entrance, and rigid "day pass" approaches can become a bottleneck if the employee has to get into the office without screening and the badge is not working.

It would be desirable to have a system and method for facilitating employee health screening that can operate without the need for additional and expensive infrastructure and avoid bottleneck issues.

Improvements in this field are therefore desired.

SUMMARY

In accordance with the presently disclosed subject matter, various illustrative embodiments of a system and method for facilitating employee health screening using an application on a mobile computing device are described herein.

In certain illustrative embodiments, a system for facilitating employee health screening using an application on a mobile computing device is provided. The system can include a memory, an electronic viewing portal with a display for viewing by an employee, and a processor coupled to the memory programmed with executable instructions, wherein the processor and/or memory are configured to receive identifying information from an employee via the electronic viewing portal, associate the employee with stored information based on the identifying information, determine one or more questions for a health screening questionnaire for the employee, display the one or more health screening questions on the display, receive answers from the employee to the health screening questions, display one or more indicators on the electronic viewing portal for viewing by the employee, and perform an employee badge activation or deactivation function based on the one or more indicators.

In certain illustrative embodiments, the processor can be configured to trigger a series of downstream processes based on the employee's responses to the questionnaire and interpret the employee's responses based on a ruleset. The processor can also be configured to update the display to indicate whether the employee is cleared or not cleared to visit the office location. The processor can be configured to communicate screening results to a badging system in real-time to facilitate the activation or deactivation of the employee's access badge for a work facility. For example, the processor can be configured to connect to a standard badging solution of the organization's facilities management/security team by leveraging application programming interfaces (APIs) or data integration mechanisms to pass screening results in real-time thereby facilitating the activation/deactivation of the employee's access badge for the facility. The processor can also be configured to communicate with a messaging system capable of sending communications to one or more of the employee and a representative of the employer regarding the screening results. For example, the processor can connect to a messaging solution capable of sending emails and SMS messages to the concerned employee/supervisor/HR personnel as applicable for the specific screening outcome.

In certain illustrative embodiments, a method for facilitating employee health screening using an application on a mobile computing device is provided. Identifying information can be received from an employee via the electronic viewing portal. The employee can be associated with stored information based on the identifying information. One or more questions for a health screening questionnaire for the employee can be determined. The one or more health screening questions can be displayed on the display. Answers can be received from the employee to the health screening questions. One or more indicators can be displayed on the electronic viewing portal for viewing by the employee. An employee badge activation or deactivation function can be performed based on the one or more indicators.

In certain illustrative embodiments, an employee can log into the user electronic viewing portal or "app" using one or more credentials (e.g., username and password) authorized by the employer's identity management system which verifies the employee's identity to be used for this application. The verified identity of the employee can be referenced against a detailed employee profile managed by specific HR systems to determine an employee profile attribute relevant for the screening solution such as the employee's primary office location, city, state, country. The solution can have a repository of rulesets stored in memory which comprise a series of health screening questions required by governing agencies in various geographic locations. The rulesets can also include business rules which help in interpreting the employee's response to each of these questions. The solution can analyze the employee's responses to the health screening questionnaire and use the applicable ruleset to determine if the employee is cleared or not cleared to visit the specific employer's office location based on those rules designed to ensure a safe workplace. Moreover, the solution can trigger a series of downstream processes based on the employee's responses to the questionnaire and interpretation of the responses based on the ruleset. The solution can also update the graphical user interface of the application to show an indicator such as green checkmark for an employee that has successfully been cleared to visit an office or a red stop sign for an employee that has not been cleared for the same purpose. The solution can trigger a series of downstream processes based on the employee's responses to the questionnaire and their interpretation based on the ruleset.

BRIEF DESCRIPTION OF THE DRAWINGS

A better understanding of the presently disclosed subject matter can be obtained when the following detailed description is considered in conjunction with the drawings and figures herein, wherein.

While the presently disclosed subject matter will be described in connection with the preferred embodiment, it will be understood that it is not intended to limit the presently disclosed subject matter to that embodiment. On the contrary, it is intended to cover all alternatives, modifications, and equivalents, as may be included within the spirit and the scope of the presently disclosed subject matter as defined by the appended claims.

DETAILED DESCRIPTION

The presently disclosed subject matter relates to a system and method for facilitating employee health screening using an application on a mobile computing device.

In certain illustrative embodiments, the system and method can provide a centralized platform for providing a health screening questionnaire for employees to fill out before visiting and/or entering an employer's facility, with one or more of the following features: tailored questions for particular regions (e.g., US states or other countries) per CDC/official guidelines, automated SMS, Email and/or employee badge activation or deactivation for missed/failed screening scenarios, and screening approval and tracking capabilities for the employee's supervisors/managers.

In certain illustrative embodiments, the system for facilitating employee health screening can include a memory, an electronic viewing portal with a display for viewing by a employee, and a processor coupled to the memory programmed with executable instructions. The processor and/or memory can be configured to receive identifying information from a employee via the electronic viewing portal, associate the employee with stored information based on the identifying information, determine one or more questions for a health screening questionnaire for the employee, display the one or more health screening questions on the display, receive answers from the employee to the health screening questions, display one or more indicators on the electronic viewing portal for viewing by the employee, and perform an employee badge activation or deactivation function based on the one or more indicators.

In certain illustrative embodiments, the method for facilitating employee health screening can include: receiving identifying information from a employee via the electronic viewing portal; associating the employee with stored information based on the identifying information; determining one or more questions for a health screening questionnaire for the employee; displaying the one or more health screening questions on the display; receiving answers from the employee to the health screening questions; displaying one or more indicators on the electronic viewing portal for viewing by the employee; and performing an employee badge activation or deactivation function based on the one or more indicators.

Figure 1:
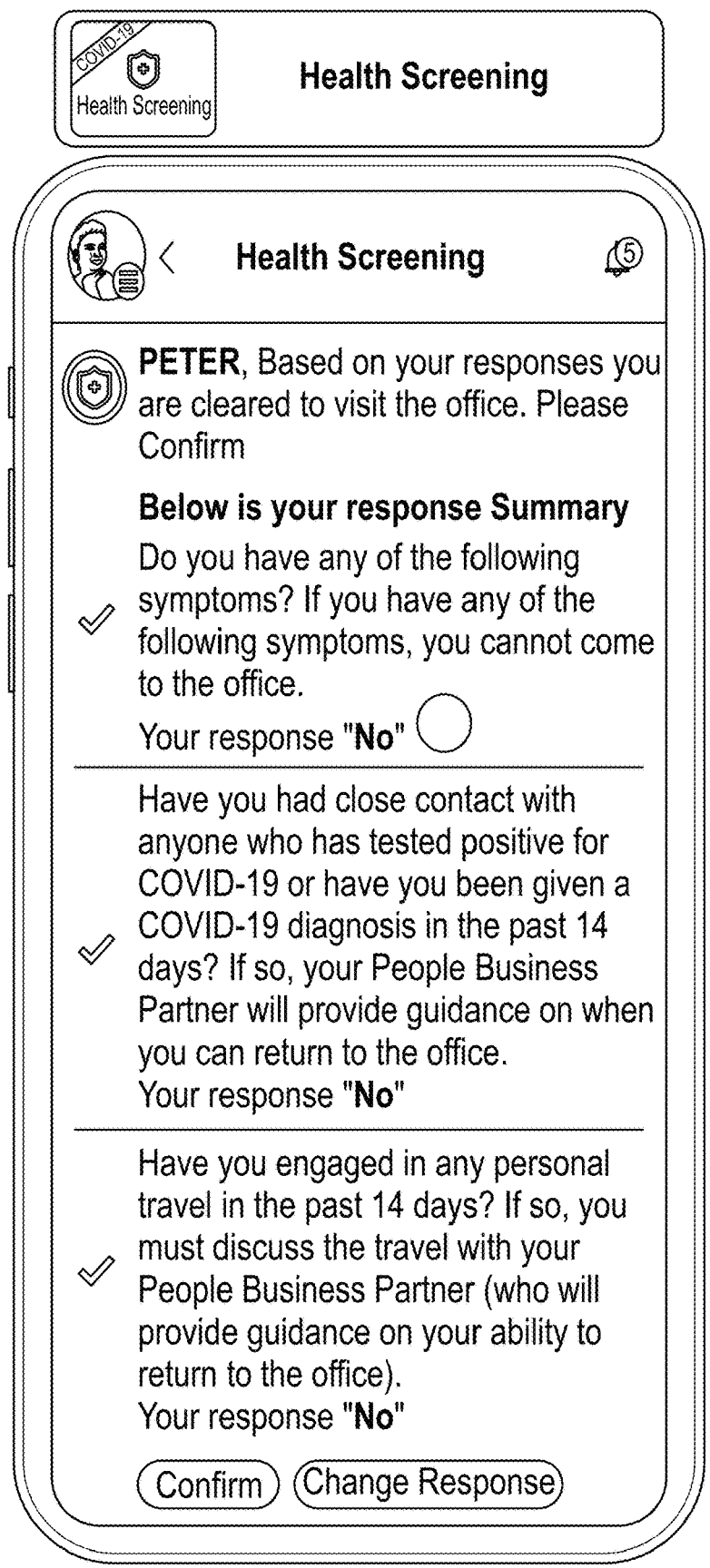
FIG. 1 is a screenshot of an application or "app" on a mobile computing device in accordance with an illustrative embodiment of the presently disclosed subject matter.

FIG. 1 shows a screenshot of an application or "app" on a mobile computing device according to illustrative embodiments of the presently disclosed system and method. The presently disclosed embodiments may utilize and/or incorporate a central server that is accessible using a variety of employee applications. The employee applications may be present in the form of downloadable applications or "apps" installable and executable on user devices, e.g., "electronic viewing portals" such as computers, smartphones, or tablets, on a real time basis. Additionally, or alternatively, the employee applications may be available as one or more web applications, accessible via a client handheld or desktop based device having an internet browser.

Figure 2:
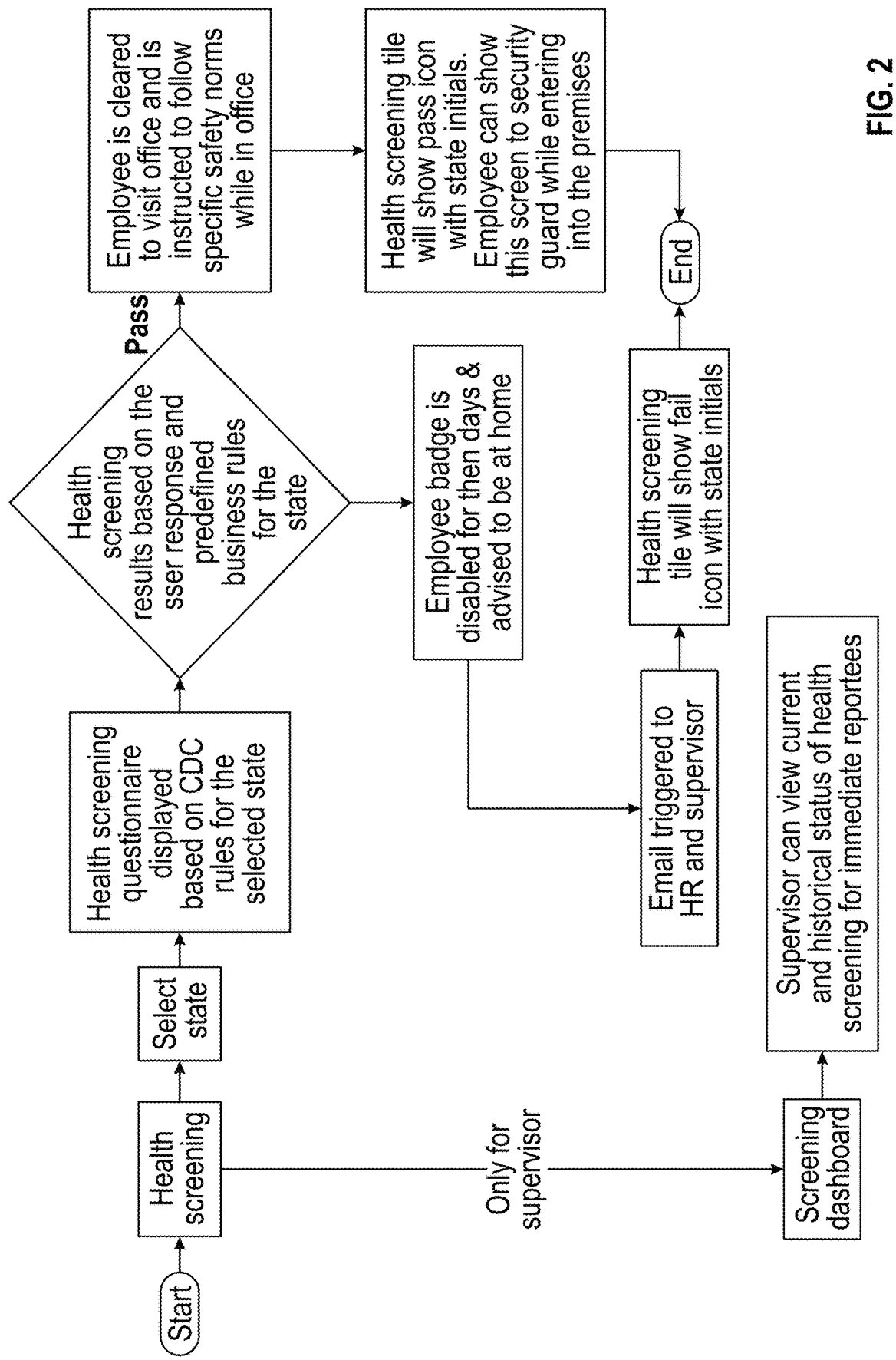
FIG. 2 is a flowchart for a series of solution steps for employee health screening in accordance with an illustrative embodiment of the presently disclosed subject matter.

FIG. 2 shows an illustrative embodiment of a process flow diagram which can be encompassed in the presently disclosed system and method, in certain illustrative embodiments.

In certain illustrative embodiments, the system and method can be used to facilitate employee health screening. For example, employees can be required to utilize the application or "solution" on a daily basis before they visit any office/facility for the employer. The application can be available in various languages to facilitate use by all employees. Rollout and availability of the application can be based upon one or more specific attributes of a local office, so for example, if certain jurisdictions do not require health screening, then those employees at the local office in that jurisdiction do not have to utilize the application. The application can include a set of questions which are tailored for employees as per their local jurisdictions, although the baseline questions would typically be similar for most users. The application can have a logic in place which uses employee office locations to determine what questions need to be cleared by the employee before he/she is permitted to visit the local site. The application can use the employee profile to determine the default state/office for the visit but the user has the flexibility to change the location in case they are planning to visit another office, e.g., an office in another state where the screening questionnaire could be different, instead of the default option. The application can request the user to acknowledge that they have approvals from their immediate supervisor to visit the office even before the screening is performed. Screening questions are set up with a conditional logic so based on the answer to the previous question, the next question is presented to the user. For example, if a question is "are you fully vaccinated?", then depending upon the response, the appropriate next question would be generated. The application can have built in logic to determine the final outcome of screening depending upon how each of the questions are answered, so that the final screen will inform the user if he/she is cleared to visit and/or enter the office or not.

Figure 3A:
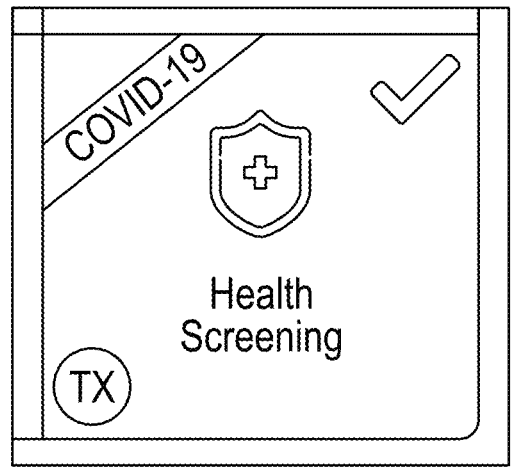
FIG. 3A is an electronically generated badge for showing that an employee has completed and cleared screening in accordance with an illustrative embodiment of the presently disclosed subject matter.

In certain illustrative embodiments, if the employee is "Cleared" to visit the office then the application can provide some useful tips to the employee such as mask mandates and social distancing norms which are periodically updated to keep up with the latest local rules. The application can also show a "Green Checkmark" (see FIG. 3A) or other like indication on the tile which can be used as a means to show that the employee completed screening in the system if security personnel would like to check that indication at the office. The checkmark can also be accompanied with the appropriate State symbol so it is clear which State specific screening the user has performed and cleared. These checkmarks can be reset every night so the employee is required to do the screening all over again the next day.

Figure 3B:
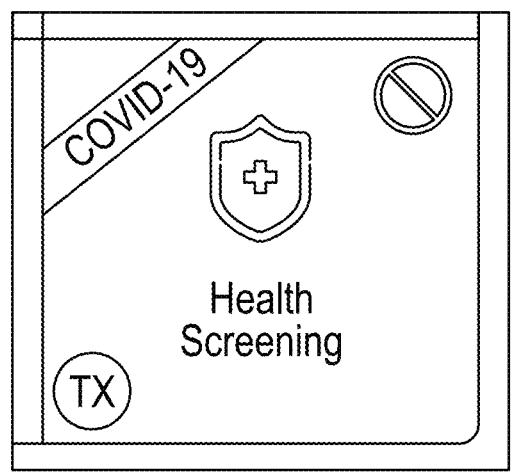
FIG. 3B is an electronically generated badge for showing that an employee has not completed and has failed screening in accordance with an illustrative embodiment of the presently disclosed subject matter.

In certain illustrative embodiments, if the employee is 'Not Cleared' to visit the office, the application can show a "Red StopSign" mark (see FIG. 3B) or like indicator indicating the employee is not permitted to be in the office facility. In this scenario, an automated alert is sent to the employee's immediate supervisor as well as the HR point of contact informing them about this person's failed screening so they can take necessary actions to not only keep the workplace safe but also to assist the employee with their situation. Additionally, this scenario also triggers an automated process by which the employee's badge is deactivated for some designated period of time (e.g., 14 days) so there is no risk of this person visiting and/or entering an office location. Then, the application can provide guidance to the employee that this is not medical advice and they should consult with a medical practitioner but for workplace safety reasons they are not permitted to visit and/or enter the office.

In certain illustrative embodiments, the solution can also include a supervisor screen where the supervisor can approve exception cases where an employee is permitted to return to work per local rules.

In certain illustrative embodiments, if an employee visits an office without completing the screening, an immediate SMS as well as Email is sent to the employee informing them that they missed the screening and should complete it immediately, or otherwise their badge access would be suspended within some designated period of time (e.g., 30 minutes). If as a follow up, the employee completes the screening than the process ends there but if they do not then after the designated time period has passed, their badge is deactivated and also a notification is sent to their Supervisor and HR contact to inform them about the situation. Once a badge is deactivated due to failed or missed screening, it requires HR intervention to restore it so that every exception is documented thereby keeping the workplace safe. The solution is also designed to protect the workplace if an employee visits the site without completing the health screening questionnaire without the need for manual checks.

In certain illustrative embodiments, a series of solution steps for the presently disclosed method can be as follows:

Step 1: Employee logs in to the Screening app. Country/state is preselected. Application pulls employee profile to determine the default office location of the employee to preselect the country/state.

Step 2: If the employee is visiting another office location, he/she can change country/state selection.

Step 3: Once the employee submits country/state, applicable questionnaire is loaded in the application. To manage questionnaire, application has: (i) question catalog of all available questions; (ii) ruleset defining various question combinations; (iii) state rule mapping which indicates which ruleset based questions are presented to the visitors in that state—per business requirements in specific cases, the rules can be even defined at county/city levels and the application be modified to even show/select county/city in addition to the country/state; (iv) as CDC and other government guidelines change very frequently, solution model can change applicable questions with a quick turnaround—e.g., as vaccines and booster shots were rolled out their validity and applicable questions changed multiple times and quite frequently as CDC gathered more scientific data; and so the solution can change such business rules very quickly to keep the app compliant with the regulations; (v) question sets are maintained in various languages to support non-English users; and (vi) if the state selected is exempt from screening than the employee is notified on the screen.

Step 4: Employee completes applicable survey questions. Questions are selected based on the applicable ruleset, although some questions are also conditional in nature and are presented based on the previous question's response. For example, if an employee indicates they tested positive for Covid, then a follow up question is asked to capture the Covid test date.

Step 5: Upon response submission, employee is informed on the application screen if they are clear or not clear to visit and/or enter an office location. Logic is maintained in the application to determine office visit clearance based on all response combinations.

Step 6: "Cleared to visit"—Employee is presented with safety instructions to follow at the office location. Application icon turns green indicating which state screening was cleared. Employee can present this screen from the phone to a security personnel at the office entrance to confirm their screening clearance. This checkmark clears out at midnight so the employee is required to redo the screening again next day Step 7: "Not Cleared to Visit"—Employee is informed in the screening application that he/she is not cleared to visit the office for specified (e.g., 10) number of days. The instructions also request the employee to provide a phone number where human resources personnel can contact them to discuss the situation. An email is triggered to the employee's supervisor and manager to inform about the failed screening case. An automated process also deactivates the employee badge for the restricted duration (e.g., 10 days) to ensure safety of other coworkers. Application icon turns red so the employee cannot go to office. Once the employee submits the screening indicating potential health issues (e.g., Covid exposure or symptoms), the application triggers a series of downstream processes. Application connects with employee's saved profile to determine the supervisor's and manager's email addresses. Application then connects to email service to trigger an email to those contacts using a predefined template informing them that the employee has failed screening. Failed screening records trigger another integration process which also makes an entry into the badging system's database providing start and stop dates for this employee's badge deactivation. In the badging system, a listening process is constantly checking for new entries in the badge deactivation request table, and as soon as a new entry is received a process is initiated in the badging system to deactivate the badge.

Step 8: "Missed screening"—If an employee visits an office without completing the screening on that day, an Email and a SMS message are sent to the employee and his/her supervisor requesting to complete the screening within 30 mins. If the screening is not completed within 30 mins, employee's badge is deactivated and the employee is informed to complete the screening and contact HR to reinstate the badge. Badging system constantly collects data when users swipe their badge at the office locations. This badging data is written to the screening application database in real-time. As entries are received in this badging table, a process constantly checks if that employee whose badge entry is received has completed screening on that day. If a new screening record is found than the process stops there. If a new screening record is not found, then a notification service is initiated to locate the employee and his/her supervisor's contact details (including email and mobile phone number) and an Email and SMS message are triggered in a predefined format. The system captures the timestamp when the notification was sent. Another system process constantly checks if a screening is now received within 30 minutes of this notification, to close this incident else if the 30 minute window is crossed then the system connects with the badging system to create a record in the badge deactivation table to deactivate the badge. In parallel, a notification is sent to the employee regarding the same.

The presently disclosed system and method have a number of advantages, as set forth in greater detail below. In addition, the presently disclosed system and method can be incorporated into the functional operations of the employer's badge recognition system and equipment, so as to communicate and provide relevant information to employers regarding employee health status prior to the employee being granted access to the employment location. This can occur on an as-needed basis, and/or on an ongoing, real time basis. As a result, the disclosed subject matter has a variety of practical applications, as well as provides solutions to a number of technological and business problems of the prior art.

In certain illustrative embodiments, the presently disclosed system and method utilize badging integration. Many existing technologies offer a QR code as the entry pass after the health screening is completed. Using those QR codes requires additional infrastructure to be setup at each work location to scan the codes so the employees can be granted entrance. The presently disclosed system and method can integrate the screening results with the badging solution so there is no additional infrastructure or process needed for entry management.

In certain illustrative embodiments, the presently disclosed system and method utilize a grace period concept for badge activity. Many existing technologies incorporate a rigid day pass approach whereby the default setting is to disable employee access and enable them only once the screening is cleared. In times of emergencies, this can become a bottleneck as well as risk to employee safety if the employee has to get in the office without screening and the badge is not working. The presently disclosed system and method can utilize a configurable grace period concept where the badge is active by default but if the employee enters a premise without completing screening than the badge can be disabled for some designated time period, e.g., within 15/30/60 mins as desired, along with a notification to the employee's supervisor. This ensures if the employee is in a genuine need to enter without screening, then the employee is able to do so.

In certain illustrative embodiments, the presently disclosed system and method utilize various built-in alert options such as Email and SMS channel to notify employees, their Supervisors, and/or their HR partners if they miss or fail screening. Having dual notification channels is also helpful in cases where part of the employee population may not have a work email address such as frontline workforce.

In certain illustrative embodiments, the presently disclosed system and method utilize HR system integration. Many existing technologies require an explicit employee registration as they do not connect with existing enterprise authentication systems. The presently disclosed system and method can utilize system integration so the users are able to use the same credentials to access the screening solution instead of a new signup.

In certain illustrative embodiments, the presently disclosed system and method utilize a robust questioning system. Many existing technologies have limitations in the questionnaires which are offered to employee and are not tailored for individual needs. The presently disclosed system and method can support a diverse international employee base which means as rules vary in US/Canada/India or even within each of States in these countries, the rules allow the solution to have different questions for screenings per the local requirements. This ensures large organizations can have a single solution which support all their office locations.

In the illustrative embodiments described herein, the system can include one or more data sources and a computer linked to a central server. Data sources may be, for example, devices configured for capturing and communicating operational data indicative of one or more operational characteristics. Data sources are configured to communicate with the central server by sending and receiving operational data over a network (e.g., the Internet, an Intranet, or other suitable network) and/or via hard wiring.

Central server may be configured to process and evaluate operational data received from data sources in accordance with employee input received via an employee interface such as the display provided on a local or remote computer or cellular or other phone or communications device, e.g., an electronic viewing portal. In certain illustrative embodiments, the communication between communications device and computer may be provided on a real-time basis. Alternatively, communication device may be configured to temporarily store or cache data and transfer the data to the central server at some later time.

In certain illustrative embodiments, computer may include a processor and software that communicates with one or more memory storage areas. Memory storage areas can be, for example, multiple data repositories which stores pre-recorded data pertaining to health screening related information. Database for data storage can be in memory storage area and/or supplementary external storage devices as are well known in the art.

While a "central server" is described herein, a person of ordinary skill in the art will recognize that embodiments of the present invention are not limited to a client-server architecture and that the server need not be centralized or limited to a single server, or similar network entity or mainframe computer system or cloud computing systems or edge computing systems or internet of things. Rather, the server and computing system described herein may refer to any combination of devices or entities adapted to perform the computing and networking functions, operations, and/or processes described herein without departing from the spirit and scope of embodiments of the present invention.

While the presently disclosed subject matter will be described in connection with the preferred embodiment, it will be understood that it is not intended to limit the presently disclosed subject matter to that embodiment. On the contrary, it is intended to cover all alternatives, modifications, and equivalents, as may be included within the spirit and the scope of the presently disclosed subject matter as defined by the appended claims.

What is claimed is:

1. A method for facilitating employee health screening using an application on a computing device, comprising:
   receiving identifying information from an employee via an electronic viewing portal operatively associated to the computing device;
   associating the employee with stored information based on the identifying information;
   determining one or more health screening questions for the employee, wherein the determining comprises:

identifying, based on stored information for the employee, a default office location for the employee;

identifying an actual office location for the employee based on either the default office location or an alternate office location provided by the employee;

requesting acknowledgement from the employee that the employee has approval from the employee's supervisor to visit the actual office location;

selecting a ruleset corresponding to the actual office location, wherein the ruleset comprises geography-specific health screening rules; and determining the one or more health screening questions based upon the selected ruleset;

displaying the one or more health screening questions on a display operatively associated to the electronic viewing portal;

receiving answers from the employee to the health screening questions;

determining, using the computing device, a screening result based on the answers from the employee;

displaying one or more indicators on the electronic viewing portal for viewing by the employee, based on the screening result; and communicating the screening result from the computing device to an employee badge in real-time, wherein the employee badge is configured to activate or deactivate based on the screening result, and wherein when the badge is activated, the employee has entry access to a work facility and when the badge is deactivated, the employee does not have entry access to the work facility.

2. The method of claim 1, wherein the employee logs in to the electronic viewing portal using one or more credentials authorized by the employer to verify the employee's identity.

3. The method of claim 2, wherein the verified identity of the employee is referenced against an employee profile to determine any employee attribute for the employee health screening.

4. The method of claim 3, wherein the application has a memory configured to store a repository of rulesets comprising a series of health screening questions required by governing agencies in various geographic locations.

5. The method of claim 4, wherein the rulesets further comprise business rules for interpreting the employee's response to the health screening questions.

6. The method of claim 1, wherein the application is configured to analyze the employee's responses to the health screening questionnaire and the screening result is a determination, based on the applicable ruleset, whether the employee is cleared to visit the specific employer's office location.

7. The method of claim 1, further comprising activating or deactivating the employee badge based on the screening result.

8. A system for facilitating for facilitating employee health screening using an application on a computing device, comprising:

a memory;

an electronic viewing portal associated with the computing device with a display for viewing by an employee; and a processor associated with the computing device and coupled to the memory programmed with executable instructions, wherein the processor and/or memory are configured to:

receive identifying information from an employee via the electronic viewing portal;

associate the employee with stored information based on the identifying information;

determine one or more questions for a health screening questionnaire for the employee, wherein the determination comprises:

identifying, based on stored information for the employee, a default office location for the employee, identifying an actual office location for the employee based on either the default office location or an alternate office location provided by the employee;

requesting acknowledgement from the employee that the employee has approval from the employee's supervisor to visit the actual office location;

selecting a ruleset corresponding to the actual office location, wherein the ruleset comprises geography-specific health screening rules, and determining the one or more health screening questions based upon the selected ruleset;

display the one or more health screening questions on the display;

receive answers from the employee to the health screening questions;

determine a screening result based on the answers from the employee;

display one or more indicators on the electronic viewing portal for viewing by the employee, based on the screening result; and communicate the screening result from the computing device to an employee badge in real-time, wherein the employee badge is configured to activate or deactivate based on the screening result, and wherein when the badge is activated, the employee has entry access to a work facility and when the badge is deactivated, the employee does not have entry access to the work facility.

9. The system of claim 8, wherein the processor is configured to trigger a series of downstream processes based on the employee's responses to the questionnaire and interpret the employee's responses based on a ruleset.

10. The system of claim 8, wherein the processor is configured to update the display to indicate whether the employee is cleared to visit the office location.

11. The system of claim 8, wherein the processor is configured to communicate with a messaging system capable of sending communications to one or more of the employee and a representative of the employer regarding the screening results.

12. The system of claim 8, further comprising activating or deactivating the employee badge based on the screening result.

* * * * *